United States Patent [19]

Adamson et al.

[11] Patent Number: 5,851,800
[45] Date of Patent: Dec. 22, 1998

[54] PROCESS FOR PRODUCING A PROTEIN

[75] Inventors: Lars Adamson, Lidingö; Erik Walum, Akersberga; Johan Dixelius, Uppsala; Kristina Lima Lie, Stockholm, all of Sweden

[73] Assignee: Pharmacia & Upjohn AB, Stockholm, Sweden

[21] Appl. No.: 852,783

[22] Filed: May 7, 1997

Related U.S. Application Data

[60] Provisional application No. 60/018,874, May 29, 1996.

[30] Foreign Application Priority Data

May 14, 1996 [SE] Sweden .................................. 9601855

[51] Int. Cl.$^6$ ............................. C12P 21/06; C12N 5/02
[52] U.S. Cl. .......................................... 435/69.1; 435/383
[58] Field of Search .................................... 435/69.1, 404, 435/383

[56] References Cited

U.S. PATENT DOCUMENTS

| | | | |
|---|---|---|---|
| 4,891,356 | 1/1990 | Szabo | 514/2 |
| 5,149,787 | 9/1992 | Kunicki et al. | 530/383 |
| 5,189,178 | 2/1993 | Galardy et al. | 548/495 |
| 5,279,939 | 1/1994 | Berka et al. | 435/6 |
| 5,296,471 | 3/1994 | Holme et al. | 514/56 |
| 5,304,603 | 4/1994 | Chemg et al. | 514/12 |
| 5,514,578 | 5/1996 | Hogness et al. | 435/325 |
| 5,514,585 | 5/1996 | Bjorn et al. | 435/254.11 |
| 5,543,396 | 8/1996 | Powers et al. | 514/9 |
| 5,589,373 | 12/1996 | Weiner et al. | 435/220 |
| 5,631,159 | 5/1997 | Marshall et al. | 435/383 |
| 5,648,237 | 7/1997 | Carter et al. | 435/69.1 |
| 5,661,034 | 8/1997 | Hayakawa et al. | 435/383 |

FOREIGN PATENT DOCUMENTS

| | | |
|---|---|---|
| 0197901 | 10/1986 | European Pat. Off. . |
| 0306968 | 3/1989 | European Pat. Off. . |
| 0319944 | 6/1989 | European Pat. Off. . |
| WO 90 02175 | 3/1990 | WIPO . |
| WO 90 05719 | 5/1990 | WIPO . |
| WO 91 09122 | 6/1991 | WIPO . |
| WO 93 10143 | 5/1993 | WIPO . |

OTHER PUBLICATIONS

M. Tokunaga et al, *Yeast* Secretion of Mouse a–Amylase from Fission Yeast Senizosaccharomyces pombe: Presence of Chymostatin–sensitive Protease Activity in the Cultate Medium, vol. 9, pp. 379–387 (1993).

Ikegawa et al, *Biochemical and Biophysical Research Communications*, Phosphoramidon, A metalloprotemase Inhibitor, Suppresses the Secretion of Endothelin–1 from Cultured Endothelial Cells by Inhibiting a Big Endothelin–1 Converting Enzyme, vol. 171, No. 2, pp. 669–675 (1990).

Mitsuo Satoh et al, *In Vitro Cell Dev. Biol*, Chinese Hamster Ovary Cells Continuously Secrete A Cysteine Endopeptidase, vol. 26, pp. 1101–1104 (Nov. 1990).

J. S. Boud et al, *Int. J. Biochem.*, Mammalian Metalloendopeptidases, vol. 17, No. 5, pp. 565–574 (1985).

Andersoon et al, *Proc. Natl. Acad. Sci.* Isolation and Characterization of Human Factor VIII: Molecular Forms in Commercial Factor VIII Concentrate, Cryoprecipitate, and Plasma, vol. 83, pp. 2979–2983 May 1986).

A. Barrett, *Methods In Enzymology* Proteolytic Enzymes: Asparatic and Metallo Peptidases: vol. 248, Academic Press, Inc., San Diego, CA, p. 263–283 (1996).

R. Kratje et al, *Journal of Biotechnology*, Evaluation of the Proteolytic Potential of in vitro–cultivated hybridoma and recombinant mammalian cells, vol. 32, pp. 107–125 (1994).

Stryer, *Biochemistry* Zymogen Activation: Digestive Enzymes and Clotting Factors, Chapter 8, WH Freeman and Co., San Francisco, CA, pp. 157–166 (1981).

N. Nishino et al, *Biochemistry*, Peptide Hydroxamic Acids as Inhibitors of Thermolysin, vol. 17, No. 14, pp. 2846–2850 (1978).

*Primary Examiner*—Jon P. Weber
*Attorney, Agent, or Firm*—Dinsmore & Shohl LLP

[57] ABSTRACT

A process is presented for reducing the detrimental influence of certain proteases on recombinant human protein and polypeptide production in a cell culture, which comprises adding an inhibitor of metal-dependent proteases or chymotrypsins to the cell culture medium. The cell culture medium for cultivating cells expressing and secreting a biologically active recombinant human polypeptide contains an inhibitor of metal-dependent proteases or chymotrypsins, or a combination thereof. Recombinant factor VIII which has been produced in a cell culture medium according to the present process is useful for the manufacture of a medicament for administration to a patient having the symptoms of hemophilia A and for treatment of hemophilia A by administration of a therapeutically effective amount of recombinant factor VIII.

19 Claims, No Drawings

PROCESS FOR PRODUCING A PROTEIN

This application is based upon provisional application Ser. No. 60/018,874, filed May 29,1996.

FIELD OF THE INVENTION

The present invention relates to a process for producing recombinant human proteins and polypeptides, and a cell culture medium for use in said production. More particularly, the invention relates to cultivating cells in a cell culture medium containing an inhibitor of metal-dependent proteases or chymotrypsins, or a combination thereof.

BACKGROUND OF THE INVENTION

Proteolytic enzymes are involved in all bodily functions, and most of them have natural regulatory counterparts, i.e. protease inhibitors. The International Commission on Enzymes has established a systematic classification and nomenclature for proteolytic enzymes: 1) serine proteinases, 2) cystein proteinases, 3) aspartic proteinases, 4) metalloproteinases, all classified according to an essential group in their active center, and finally 5) a subclass of proteinases with catalytic mechanism yet unknown (Borivoj Keil, *Specificity of Proteolysis,* Springer-Verlag NY, 1992, 336 pages). The intention of this classification is not functional, neither is it related to the biological source of the enzyme at issue. The problem of classification of proteolytic enzymes, often abbreviated proteases, is described in the introduction chapter: "The Classification of enzymes in Enzyme Nomenclature (1200) is made according to the reactions they catalyze. Thus rule can hardly be applied for endopeptidases. The overall reaction catalyzed by this large group of enzymes is essentially always the same: cleavage of a peptide bond. A protein, however, cannot be considered as a substrate in the classical term: it contains hundreds of potential substrates, a set of qualitatively different peptide bond types with varying quantitative representation. Moreover, the availability of these bonds vary according to the overall conformation of the polypeptide chain. Therefore, the Enzyme Nomenclature makes an exception of endopeptidases from its rule: instead of classification according to the catalyzed reaction, endopeptidases are classified by the type of their active site. In this way, enzymes with completely different specificity (like trypsin, chymotrypsin and prolyl peptidase) are found in the same group." As further illustrated in the same reference, the substrate and inhibitor specificity is far more complicated than a simple relation to five classes of enzymes. Nevertheless, this classification is widely used in the literature, for example when various effects of proteolysis are to be described.

In serine proteases a serine moiety is essential for the activity, i.e. the cleavage function. The specificity of different serine proteases is based on the features of the cavities fitting the structures of corresponding substrates. A deep cleft accounts for the specificity of chymotrypsin for aromatic and other bulky hydrophobic side chains (see L. Stryer, *Biochemistry,* W. H. Freeman and Co., San Francisco, Calif., USA, 1981 pp. 157–166).

Many proteases need alkaline-earth metals or metals (in the following just denoted metals) for their activity. The metal-dependent proteases are either considered to be metal-activated proteases (to which metal ions must be added for activity) or metallo proteases (which contain metals as an integral part of their structure). Concerning the first group, activation and stabilization of enzymes by metals frequently occur in several classes of proteases, such as serine and cysteine proteases.

The importance of a metallo protease in cultured endothelial cells for the secretion of a certain metabolite has been shown by R. Ikegawa et al., *Biochem. Biophys. Res. Comm.* 171(2), pp. 669–675 (1990). This was revealed by the suppressing effect on this secretion recognized by the addition of a metallo protease specific inhibitor. It was evident, however, that the enzyme was confined to the intracellular space, since no effect of the inhibitor was obtained in a cell-free conditioned medium.

The effect of proteases are far more often mentioned in the context of the potential risk of degradation of the protein at issue.

The effect of proteases in cultures of CHO cells has been studied by M. Satoh et al., *In Vitro Cell Dev. Biol.,* 26, pp. 1101–1104 (1990). Various inhibitors were used to classify the proteolytic activity present. It was concluded from the lack of inhibition by addition of phosphoramidon that the proteases did not belong to the metallo proteases, at least not to those generally known to be inhibited by this agent. The effect of the other inhibitors added revealed that the extracellular proteolytic activity arose from cysteine proteases.

Another study describes the proteolytic profiles for BHK cells and hybridoma cultures respectively (RB Kratje et al., *J. Biotechnol.,* 32, pp. 107–125 (1994)). No activity of metallo proteases was found with any of these cell types. Activity corresponding to several serine proteases was however identified. It was also disclosed that the presence of proteases was dependent not only on the type of cells used but also on the culture conditions and the age of the culture.

From the above mentioned papers, it is evident that a stable secretion of polypeptides in cell cultures may be impaired by a variety of proteolytic enzymes. For an efficient control of these degrading forces, versatile tools are needed. By such a control, the homogeneity of the target protein would be better retained. Moreover, protein additives or substances produced endogenously by the cells, susceptible to proteolytic attack, would be protected. All together, a higher performance and consistency of the process as a whole would be achieved.

Tokunaga et al, *Yeast,* Vol. 9 (1993), pp. 379–387 relates to chymostatin-sensitive protease activity in the cell culture medium of *Schizosaccharomyces pombe* which digests α-amylase secreted into the culture medium. Tokunaga et al. only disclose mouse α-amylase. Furthermore, *Schizosaccharomyces pombe* is a fission yeast and α-amylase is an enzyme, more particularly a carbohydrate-degrading enzyme.

EP-A2-319944 to Zymogenetics relates to co-expression in eukaryotic cells of a desired protein, e.g. t-PA, factor VII or factor IX, and a protein which processes or stabilizes the desired protein, e.g. a protease inhibitor. In this case, therefore, the protease inhibitor is produced in-situ. This necessitates the introduction of a first DNA sequence encoding the desired protein, and at least one additional DNA sequence encoding the stabilizing protein.

WO-A-9002175 to Novo-Nordisk discloses a method for producing polypeptides by culturing eukaryotic cells in the presence of various protease inhibitors. Specific examples include factor VIII as the polypeptide, but the protease inhibitors are all directed to serine and cysteine proteases.

In EP-A-306 968 to Chemo-Sero-Therapeutic Res. Inst. and Teijin, use is made of aprotinin in a cell culture medium used for producing a deletion derivative of factor VIII. The expression level after addition of 100 to 10,000 KIU/ml was stated to be two to three times higher than the control without addition of aprotinin.

The problems encountered with metal-dependent proteases and chymotrypsins in the production of various proteins has been much less surveyed than the role of cysteine and serine proteases, especially in literature covering mammalian cell cultures. More particularly, the specific problem with metal-dependent proteases and chymotrypsins has never been addressed previously in connection with factor VIII.

Various solutions have been suggested to reduce the degradation by proteases of proteins and polypeptides, e.g. plasma derived as well as recombinant factor VIII molecules. These solutions have been directed to reduce the influence of serine and cysteine proteases in general. Serine and cysteine proteases are considered to be the most detrimental ones in blood plasma as well as in cell cultures. Thus, WO-A-9310143 to Johnson et al discloses a method for recovering a purified and stabilized protein by contacting biological sample containing factor VIII with at least one protease inhibiting or protease removing agent. The method is particularly directed to inhibit or remove thrombin, since factor VIII is said to be very sensitive to minute quantities of this serine protease naturally present in blood plasma. The protease inhibitors include, e.g., benzamidine, antithrombin III, heparin and hirudin. The effect of the method is only shown for plasma derived factor VIII.

The aim of the present invention is to provide a solution to the problems encountered with proteases in general, and more particularly with metal-dependent proteases and chymotrypsins in cell culture media used for producing recombinant proteins and polypeptides, especially factor VIII.

SUMMARY OF THE INVENTION

Proteases generally tend to reduce the activity of proteins and polypeptides by degrading the molecule. The present invention relates to a process for reducing the detrimental influence of certain proteases on recombinant protein and polypeptide molecules, by adding an inhibitor of metal-dependent proteases or chymotrypsins to the cell culture medium. The presence of the specific protease inhibitor of the present invention allows for a prolonged harvest period and considerably higher yield with essentially retained protein and polypeptide activity. The invention also relates to a cell culture medium for cultivating cells expressing and secreting a biologically active recombinant polypeptide containing an inhibitor of metal-dependent proteases or chymotrypsins, or a combination thereof. The invention further relates to use of recombinant factor VIII which has been produced in a cell culture medium according to the present process for the manufacture of a medicament for administration to a patient having the symptoms of hemophilia A. Also, the invention relates to a method for treatment of hemophilia A by administration of a therapeutically effective amount of recombinant factor VIII which has been produced in a cell culture medium according to the present process.

DETAILED DESCRIPTION OF THE INVENTION

An object of the present invention is to reduce the influence of metal-dependent proteases and chymotrypsins when cultivating host cells for producing recombinant polypeptides.

Another object of the present invention is to provide efficient cultivation conditions, thereby essentially retaining the activity of the recombinant polypeptides.

A further object of the present invention is to increase the half-life of the proteinaceous supplements added to the cell culture medium and other proteins produced by the cells and secreted in the culture medium.

The objects above are met by the present invention, which relates to a process for producing a biologically active recombinant human polypeptide in a cell culture medium allowing expression and secretion of said polypeptide, wherein an inhibitor of metal-dependent proteases or chymotrypsins, or a combination thereof, is added to the cell culture medium.

The present invention further relates to a cell culture medium for cultivating cells expressing and secreting a biologically active recombinant human polypeptide, wherein the cell culture medium contains an inhibitor of metal-dependent proteases or chymotrypsins, or a combination thereof.

The present invention also relates to a method of cultivating cells expressing a recombinant human polypeptide in a cell culture medium, wherein the cell culture medium contains an inhibitor of metal-dependent proteases or chymotrypsins, or a combination thereof. The present invention further relates to a method of producing a recombinant human polypeptide, by cultivating cells expressing the recombinant human polypeptide in a cell culture medium containing an inhibitor of metal-dependent proteases or chymotrypsins, or a combination thereof, and recovering the polypeptide.

The inventors of the present invention have found that certain protease inhibitors have a surprisingly positive impact on the activity of polypeptides during cultivation of host cells expressing recombinant polypeptides. The presence of these inhibitors results in higher productivity. In this way, the yield of polypeptide with essentially retained activity and/or homogeneity can be increased considerably.

The inhibitors of metal-dependent proteases and chymotrypsins are suitably compounds containing a hydrophobic moiety. The chymotrypsins differ from other serine protease by the presence of a deep cleft in the active site. This deep cleft accounts for the substrate specificity encountered with chymotrypsins. Therefore, suitably the hydrophobic moiety is an aromatic, a heterocyclic aromatic or another bulky side group. Heterocyclic aromatic side groups relate to aromatic compounds in which an element other than carbon is present in the aromatic ring. Examples are pyridine, pyrrole, furan and thiopene. Furthermore, in the present invention, the term hydrophobic bulky side group relates to various other non-polar ring structures such as monocycloalkanes, e.g. cyclohexane, dicycloalkanes and polycycloalkanes, or substituted derivatives of any of these structures.

The metal-dependent proteases are either considered to be metal-activated proteases (to which metal ions must be added for activity) or metallo proteases (which contain metals as an integral part of their structure). Concerning the first group, activation and stabilization of enzymes by metals frequently occur in several classes of proteases, such as serine and cystein proteases. For example, in the field of blood functions, especially coagulation, fibrinolysis, and complement activation, a group of vitamin K-dependent calcium-binding domains are common (see e.g. László Patthy, *Methods in Enzymology*, 222, pp. 10–21 (1993)). Concerning the latter metallo proteases, a review of mammalian metalloendopeptidases, being an important subgroup of this protease class, can be found in Bond et al, *Int. J Bio-chem.*, 17, No. 5, pp. 565–574 (1985). These authors conclude that $Zn^{2+}$ appears to be the essential metal for all of the characterized mammalian metallo proteases. In a more recent review (D. A. Auld, *Methods in Enzymology*, 248, pp. 229–242 (1995)), this ion is still considered to be the active ion of an overwhelming majority of the metallo proteases. This does not exclude a structural and functional role also of other metals, like $Cu^{2+}$, $Fe^{2+}$, $Fe^{3+}$, $Mn^{2+}$, $Co^{2+}$ and $Cd^+$ (Auld, see above). Thus, an enzyme dependent on $Zn^{2+}$ as well as $Ca^{2+}$, is described in Butler et al, Biochem. J., 241, pp. 229–235 (1987).

In the present invention, the inhibitors of metal-dependent proteases can be compounds structurally related to the natural substrate of the protease and containing an electronegative moiety. Such compounds are suitably peptides, peptide analogues or other compounds mimicking a part of the natural substrate, preferably selected from the group consisting of phosphoramidates, hydroxamates and carboxylates. The mechanism for the inhibition of metallo proteases by peptides or peptide analogues functionalized with, e.g., phosphoramidates, hydroxamates or carbonyl groups is not fully clear. However, in the literature their effect is considered to be due to a chelating function (see especially pp. 221–222 of Birkedal-Hansen et al, *Critical Review in Oral Biology and Medicine*, 4(2), pp. 197–250 (1993)).

Structurally related compounds can be natural, as in the case of phosphoramidon, or synthetic. The design of such synthetic inhibitors is reviewed in Bond et al (see above). One example, described by N. Nishino and J. C. Powers, *Biochemistry*, 17 (14), pp.2846–2850 (1978), is the synthesis of specific inhibitors for the zinc metalloendopeptidase thermolysin. In this case, the specificity of the inhibitor peptide analogue was achieved by including a hydrophobic amino acid, intended for interaction with a corresponding pocket in the active site of the enzyme, as well as a hydroxamic acid residue, for interaction with the zinc atom. An illustration of this phenomenon is given in B. Roques et al, *Methods in Enzymology*, 248, pp. 263–283, especially pp. 268–269 and 272 (1995)). Further examples of hydroxamates are disclosed in WO 90/05719.

The phosphoramidates suitable for use in the present invention can be natural or synthetic. Phosphoramidon is a natural phosphoramidate preferably used in the present invention. Phosphoramidon inhibits the action of thermolysin a metalloendopeptidase. The structure of this phosphoramidate is N-(α-L-rhamnopyranosyloxyhydroxyphosphinyl)-L-leucyl-L-tryptophan), abbreviated Rha-P-Leu-Trp.

The residue P-Leucine-Tryptophan present in phosphoramidon is a common feature for several phosphoramidates. Data from various sources indicate that this residue constitutes the active group e.g. in phosphoramidon. Therefore, in the present invention use is suitably made of compounds containing the residue P-Leucine-Tryptophan.

The concentration of the inhibitor of metal-dependent proteases can be in the range of from about 5 nM up to about 5 mM, suitably in the range of from 0.5 µM up to 2 mM, and preferably in the range of from 1 µM up to 1 mM.

Chymotrypsins are serine proteases. In the present invention, chymotrypsins relate to chymotrypsins and chymotrypsin-like proteases. Chymotrypsin-like proteases here relate to proteases with a function and/or chemical structure closely resembling that of chymotrypsins. In the following, chymotrypsin is used to designate chymotrypsins as well as chymotrypsin-like proteases. A connection between chymotrypsins and a metallo protease is revealed in Borivoj Keil, *Specificity of Proteolysis* (see above), Table 11, pp. 36–39. In a classification according to preferred sequences of amino acids in the cleavage site, chymotrypsin is grouped together with other proteases cleaving at LYL (Leucine, Tyrosine, Leucine). Among the other enzymes of this group is a collagenase, an enzyme usually referred to as a metallo protease.

The inhibitor of chymotrypsins can be natural or synthetic, and structurally related to the natural substrate of the protease. The inhibitor of chymotrypsins suitably contains a hydrophobic moiety. The functionality of a hydrophobic moiety is a property shared with the specific inhibitors for the zinc metalloendopeptidase thermolysin mentioned in a previous paragraph. The inhibitor of chymotrypsins is suitably selected from the natural compounds chymostatin A, chymostatin B or chymostatin C, or any mixture thereof. Commonly, chymostatin is a mixture containing all three chymostatins, chymostatin A constituting the major portion. All chymostatins contain a residue of the unusual amino acid α-(2-iminohexahydro-4(S)-pyrimidyl)-S-glycine. The structure of these natural compounds are N-[(S)-1-carboxy-2-phenylethyl]carbamoyl-α-N-[2-iminohexahydro-4(S)-pyrimidyl]-S-glycyl-L-leucyl-phenylalaninal (Chymostatin A), N-[(S)-1-carboxy-2-phenylethyl]-carbamoyl-α-N-[2-iminohexahydro-4(S)-pyrimidyl]-S-glycyl-L-valyl-phenylalaninal (Chymostatin B), and N-[(S)-1-carboxy-2-phenylethyl]-carbamoyl-α-N-[2-iminohexahydro-4(S)-pyrimidyl]-S-glycyl-L-isoleucylphenylalaninal (Chymostatin C).

The concentration of the compound inhibiting chymotrypsins can be in the range of from about 0.001 µg/L up to 100 mg/L, suitably in the range of from 0.01 µg/L up to 25 mg/L, and preferably in the range of from 0.1 µg/L up to 100 µg/L. The above given figures are equal to a concentration of the compound inhibiting chymotrypsins in the range of from about 1.67 pM up to about 167 µM, suitably in the range of from 16.7 pM up to 41.7 µM, and preferably in the range of from 167 µM up to 167 nM.

The host cells for use in the present invention can be procaryotic or eucaryotic, suitably eucaryotic cells. The host cells for use in the present invention can be mammalian, bacterial, fungal or insect cells. The cells are suitably mammalian cells or insect cells, preferably mammalian cells. The insect cells can be SF-9 or SF-21 cells. The mammalian cells can be Chinese Hamster Ovary (CHO) cells, Baby Hamster Kidney (BHK) cells, COS cells or hybridoma cells, preferably CHO cells.

The cell culture medium may contain serum. Suitably, however, the cell culture medium is a low-serum medium, and preferably a serum-free medium. The cell culture medium may further contain one or more added proteins, such as human serum albumin (HSA), bovine serum albumin (BSA), insulin, growth factors, IGF-1, IGF-2, growth hormone, neurotrophines, leptin, transferrin and the von Willebrand factor (vWf). If proteins are added to the cell culture medium in the present invention, such proteins are preferably produced by recombinant DNA techniques. Preferably, the cell culture medium is a protein-free medium, i.e. free of added proteinaceous substances. This makes possible production of a polypeptide with a very high specific activity. In this way, the medium will be well defined and the risk of introducing contaminants such as mycoplasma, bacteriophages, virus and toxins will be almost extinguished. Additionally, the down-stream purification of the polypeptide molecules produced will be facilitated.

The cell culture medium may be based on a complete medium, or a nutrient basal medium supplemented by a number of components. Examples of suitable complete media are various ASF media marketed by Ajinomoto of Japan, Dulbecco's Modified Eagle Medium (DMEM), Eagle's Minimum Essential Medium, Ham's Medium F-12 and RPMI-1640 Medium. Various combinations of DMEM and Ham's F-12, both marketed by GIBCO of Renfrewshire, Scotland, are also suitable complete mediums for use in the present invention. A supplemented basal medium may be prepared by adding components to the nutrient basal medium in accordance with standard procedures for preparing cell culture media.

Supplements added to the cell culture medium are not critical to the present invention and may be combinations of those known in the art which are suitable for the cells at issue. Examples of supplements that can be used include insulin, transferrin, ascorbic acid, ethanolamine, glutamine and sodium selenite.

The protease inhibitor can be added to the cell culture medium once, several times or continuously during the cultivation period. The inhibitors of the present invention are suitably added to the cell culture medium at change of medium. The protease inhibitor can be a mixture of an inhibitor of metal-dependent protease and an inhibitor of chymotrypsins. The protease inhibitor can also be a combination of an inhibitor of metal-dependent proteases and an inhibitor of chymotrypsins, added in arbitrary sequence.

In the present invention, polypeptides refer to proteins and oligopeptides with at least 20 amino acids in the chain. The number of amino acids of the polypeptide produced according to the present invention, suitably lies in the range of from 30 up to 4,500 amino acids, and preferably in the range of from 40 up to 3,000 amino acids. Polypeptides which can be produced according to the present invention include polypeptides exhibiting coagulant, anticoagulant and fibrinolytic activities, membrane bound and nuclear receptors, and metabolism regulating humural factors (hormones). Specific examples of polypeptides that can be produced according to the present process are factor VIII, factor V, factor VII, factor IX, tPA, prostaglandin receptors, glucocorticoid receptors, peroxisome proliferator activated receptors (PPARs), factors promoting growth and cell survival, interleukin, interferon and IGF binding proteins (IGFBP). The polypeptides can be full-length, i.e. the sequence of amino acids is identical to the corresponding sequence found in mammals in general, and in human beings in particular. The polypeptides can also be deletion derivatives of the full-length polypeptides, where one or more amino acids are missing. In the present invention, the polypeptide is preferably factor VIII.

In the present invention, the factor VIII produced by recombinant DNA technique can be full-length factor VIII or preferably a deletion derivative of full-length factor VIII having coagulant activity. By deletion derivative is here meant coagulation factor VIII in which the whole or part of the B-domain is missing, while the coagulant activity is retained. The remaining domains are suitably linked by an amino acid linker. Examples of various linker constructions are given in P. Lind et al, *Eur. J. Biochem.*, Vol. 232 (1995), pp. 19–27. The structure and biochemistry of recombinant factor VIII products in general have been described by Kaufman, *Trends in Biotechnology*, 9, pp. 353–359 (1991) and *Hematology*, 63, pp. 155–65 (1991).

Full-length factor VIII present in human plasma has a molecular mass of about 300 kDa. Factor VIII concentrates derived from such plasma contain several fragmented fully active factor VIII forms as described by Andersson et al, *Proc. Natl. Acad. Sci. USA*, 83, pp. 2979–83 (May 1986). The smallest active form has a molecular mass of about 170 kDa and consists of two chains of about 90 kDa and about 80 kDa held together by metal ion(s). Reference is here made to EP-A-0 197 901 (Pharmacia AB). The biologically active factor VIII produced according to the present invention, therefore, suitably has a molecular mass in the range of from about 170 kDa up to about 300 kDa.

Pharmacia AB of Stockholm, Sweden, has developed a recombinant factor VIII product which corresponds to the about 170 kDa plasma factor VIII form in therapeutic factor VIII concentrates. The truncated recombinant factor VIII molecule is termed r-VIII SQ and is produced by Chinese Hamster Ovary (CHO) cells in a cell culture process in serum-free medium. The structure and biochemistry of r-VIII SQ have been described in WO-A-9109122 (Pharmacia AB). In the present invention, more preferably the deletion derivative is recombinant factor VIII SQ (r-VIII SQ).

The recombinant factor VIII produced in a cell culture medium according to the present process can be used for the manufacture of a medicament for administration to a patient having the symptoms of hemophilia A. Also, the invention relates to a method for treatment of hemophilia A by administration of a therapeutically effective amount of recombinant factor VIII which has been produced in a cell culture medium according to the present process.

The pH of the cell culture medium suitably lies in the range of from about 6 up to about 8. The osmolality of the cell culture medium suitably lies in the range of from about 280 up to about 400 milliosmoles.

The cell culture technique can be suspension culture, monolayer culture such as roller bottle, microcarriers or hollow fiber, preferably suspension culture technique.

The mode of operation of the present process can be continuous or batch-wise.

The following Examples are provided for purposes of illustration only and are not to be construed as in any way limiting the scope of the present invention, which is defined by the appended claims.

The percentages and parts are per weight, unless otherwise stated.

EXPERIMENTAL

Preparation of Recombinant Factor VIII

The production of recombinant factor VIII SQ (r-VIII SQ) was essentially performed as described in patent WO-A-

9109122 to Pharmacia & Upjohn, Examples 1 to 3. A DHFR deficient CHO cell-line (DG44) was electroporated with an expression vector containing the r-VIII SQ gene and an expression vector containing the dihydrofolate-reductase gene. Following selection on selective media, surviving colonies were amplified through growth in stepwise increasing amounts of methotrexate. Supernatant from the resulting colonies were individually screened for factor VIII activity. A production clone was chosen and this was subsequently adapted to serum-free suspension growth in a defined medium.

Material

The chymostatin used in the experiments, contained chymostatin A, chymostatin B and chymostatin C, chymostatin A constituting the major portion. The protease inhibitors were all of analytical grade and obtained from Sigma in St. Louis, USA.

Analytical Methods

The activity of coagulation factor VIII was assessed by a chromogenic substrate assay (Coatest Factor VIII, Chromogenix AB, Mölndal, Sweden). Activated factor X (Xa) is generated via the intrinsic pathway where factor VIII acts as co-factor. Factor Xa is then determined by the use of a synthetic chromogenic substrate, S-2222 in the presence of a thrombin inhibitor I-2581 to prevent hydrolysis of the substrate by thrombin. The reaction is stopped with acid, and the VIII:C, which is proportional to the release of pNA (para-nitroaniline), is determined photometrically at 450 nm against a reagent blank. The unit of factor VIII:C is expressed in international units (IU) as defined by the current International Concentrate Standard (IS) established by WHO.

The cell viability was determined on several occasions as disclosed in Tables I–IV in order to verify that the added inhibitors had no negative effect on the cell survival throughout the entire production period. The analyses were made after staining the cells with Erythrosin B in a Bürker chamber or by flow cytometry. The portion of viable cells was calculated in relation to the total number of cells (%).

EXAMPLE 1

This example is intended to illustrate the efficiency of the present invention as compared to various other protease inhibitors.

CHO cells were cultivated under growth conditions in spinner flasks in a complete culture medium such as ASF or a mixture of DMEM and Ham's Medium F-12. Initially, the temperature was 37° C. and the cell content was about $0.7 \times 10^6$ cells/ml of cell culture medium. Day 0 was defined as the day of commenced production. The temperature was lowered to 34° C. On day 3, the culture medium was placed by a fresh medium including 0.5 mM of butyric acid, and the cell content was adjusted to about $3 \times 10^6$ cells/ml of cell culture medium. On day 4, a suspension of the cells in production was alequoted to polypropylene tubes for continuous cultivation and the protease inhibitors were added. On day 5, the medium was replaced and the protease inhibitors added. Replacement of medium was performed on day 6, day 7, day 10 (accumulated value after 72 hours). On day 11, the experiments were stopped. Western Blot analysis revealed that the quality of the factor produced was essentially unaffected. The viability was generally high. The lowest value, 90% obtained for the control and aprotinin, on production day 11.

The results are given in the following Tables I–IV.

TABLE I

Factor VIII: C in cell culture medium containing protease inhibitors according to the invention

| Test | Inhibitor, concentration | Day 6, IU/ml | Day 6, % | Day 7, IU/ml | Day 7, % | Day 10, IU/ml | Day 10, % | Day 11, IU/ml | Day 11, % | Accumulated, IU/ml | Accumulated, % |
|---|---|---|---|---|---|---|---|---|---|---|---|
| 1 | Control | 2.93 | 100 | 7.2 | 100 | 24.5 | 100 | 12.5 | 100 | 47.1 | 100 |
| 2 | Phosphoramidon, 0.015 mM | 4.93 | 168 | 11.0 | 152 | 34.5 | 141 | 15.1 | 121 | 65.6 | 139 |
| 3 | Phosphoramidon, 0.15 mM | 6.12 | 209 | 10.2 | 141 | 39.0 | 159 | 17.1 | 137 | 72.4 | 154 |
| 4 | Chymostatin, 1.04 nM (0.625 µg/l) | 5.48 | 187 | 12.5 | 174 | 33.7 | 138 | 15.7 | 126 | 67.4 | 143 |
| 5 | Chymostatin, 10.4 nM (6.25 µg/l) | 6.80 | 232 | 10.6 | 148 | 38.5 | 157 | 10.7 | 86 | 66.6 | 141 |

TABLE II

Factor VIII: C in cell culture medium containing protease inhibitors not according to the invention

| Test | Inhibitor, concentration | Day 6, IU/ml | Day 6, % | Day 7, IU/ml | Day 7, % | Day 10, IU/ml | Day 10, % | Day 11, IU/ml | Day 11, % | Accumulated, IU/ml | Accumulated, % |
|---|---|---|---|---|---|---|---|---|---|---|---|
| 1 | Control | 2.93 | 100 | 7.2 | 100 | 24.5 | 100 | 12.5 | 100 | 47.1 | 100 |
| 2 | Aprotinin, 0.3 µM | 3.83 | 131 | 8.52 | 118 | 24.5 | 100 | 15.5 | 124 | 52.3 | 111 |
| 3 | Aprotinin, 3.0 µM | 3.96 | 135 | 8.42 | 117 | 24.1 | 98 | 13.8 | 110 | 50.3 | 107 |

TABLE II-continued

Factor VIII: C in cell culture medium containing protease inhibitors not according to the invention

| Test | Inhibitor, concentration | Day 6, IU/ml | Day 6, % | Day 7, IU/ml | Day 7, % | Day 10, IU/ml | Day 10, % | Day 11, IU/ml | Day 11, % | Accumulated, IU/ml | Accumulated, % |
|---|---|---|---|---|---|---|---|---|---|---|---|
| 4 | Chloroquine, 0.625 µM | 4.19 | 143 | 9.39 | 130 | 26.5 | 108 | 11.4 | 91 | 51.5 | 109 |
| 5 | Chloroquine, 6.25 µM | 3.75 | 128 | 7.19 | 100 | 25.5 | 104 | 9.41 | 75 | 45.9 | 97 |
| 6 | L-Histidine, 0.52 mM | 3.17 | 108 | 6.22 | 86 | 23.1 | 94 | 11.5 | 92 | 43.9 | 93 |
| 7 | L-Histidine, 5.2 mM | 2.17 | 74 | 4.64 | 64 | 8.16 | 33 | 3.37 | 27 | 18.3 | 39 |

TABLE III

Cell viability in cell culture medium containing protease inhibitors according to the invention

| Test | Inhibitor, concentration | Day 6, % | Day 7, % | Day 10, % | Day 11, % |
|---|---|---|---|---|---|
| 1 | Control | 97.4 | 97.5 | 91.4 | 90.7 |
| 2 | Phosphoramidon, 0.015 mM | 98.6 | 96.5 | 89.1 | 94.7 |
| 3 | Phosphoramidon, 0.15 mM | 98.8 | 96.7 | 91.3 | 93.1 |
| 4 | Chymostatin, 1.04 nM (0.625 µg/l) | 98.3 | 98.0 | 94.9 | 93.6 |
| 5 | Chymostatin, 10.4 nM (6.25 µg/l) | 95.3 | 95.9 | 91.6 | 94.0 |

TABLE IV

Cell viability in cell culture medium containing protease inhibitors not according to the invention

| Test | Inhibitor, concentration | Day 6, % | Day 7, % | Day 10, % | Day 11, % |
|---|---|---|---|---|---|
| 1 | Control | 97.4 | 97.5 | 91.4 | 90.7 |
| 2 | Aprotinin, 0.3 µM | 97.7 | 98.4 | 93.8 | 89.4 |
| 3 | Aprotinin, 3.0 µM | 97.8 | 98.1 | 94.1 | 90.1 |
| 4 | Chloroquine, 0.625 µM | 98.0 | 95.3 | 90.1 | 92.5 |
| 5 | Chloroquine, 6.25 µM | 96.9 | 98.2 | 94.5 | 90.3 |
| 6 | L-Histidine, 0.52 mM | 98.0 | 98.0 | 92.5 | 92.8 |
| 7 | L-Histidine, 5.2 mM | 99.1 | 97.8 | 95.4 | 95.4 |

As is evident from Table I, the presence of protease inhibitors according to the present invention dramatically increases the possibility of retaining factor VIII:C. As is evident from Table II, the presence of various other protease inhibitors have a very small or even negative effect on factor VIII:C. From Table III it is evident that the increased production of factor VIII illustrated in Table I cannot be attributed to an increased or decreased cell viability. Furthermore, from Table IV it is evident that the lack of effect on production of factor VIII illustrated in Table II is not an effect counteracting a decreased cell viability.

We claim:

1. A process for producing a biologically active recombinant human polypeptide in a cell culture allowing expression and secretion of said polypeptide into the cell culture medium, comprising adding an inhibitor of metal-dependent proteases containing a phosphoramidate, hydroxamate or carboxylate, or an inhibitor of chymotrypsins containing α-(2-iminohexahydro-4(S)-pyrimidyl)-S-glycine, or a combination thereof, to the cell culture medium, and recovering said polypeptide from the cell culture medium.

2. The process according to claim 1, wherein the inhibitor of metal-dependent proteases or chymotrypsins contains an aromatic, heterocyclic aromatic or another bulky side group.

3. The process according to claim 1, wherein the metal-dependent protease is a metallo protease.

4. The process according to claim 1, wherein the metal ion required for activity of the metal-dependent protease is selected from the group consisting of $Zn^{2+}$, $Cu^{2+}$, $Fe^{2+}$, $Fe^{3+}$, $Mn^{2+}$, $Co^{2+}$ and $Cd^{2+}$.

5. The process according to claim 1, wherein the inhibitor of metal-dependent proteases is phosphoramidon.

6. The process according to claim 5, wherein the concentration of phosphoramidon ranges from about 5 nM to about 5 mM.

7. The process according to claim 6, wherein the concentration of the inhibitor of metal-dependent proteases ranges from 1 µM to 1 mM.

8. The process according to claim 1, wherein the inhibitor of chymotrypsins containing α-(2-iminohexahydro-4(S)-pyrimidyl)-S-glycine is selected from the group consisting of chymostatin A, chymostatin B, chymostatin C, and mixtures thereof.

9. The process according to claim 1, wherein the concentration of the inhibitor of chymotrypsins ranges from about 0.001 µg/L, to about 100 mg/L.

10. The process according to claim 9, wherein the concentration of the inhibitor chymotrypsins ranges from 0.1 µg/L to 100 µg/L.

11. The process according to claim 1, wherein the cell in the cell culture is a mammalian, bacterial or insect cell.

12. The process according to claim 11, wherein the cell is a mammalian cell.

13. The process according to claim 12, wherein the mammalian cell is selected from the group consisting of Chinese Hamster Ovary (CHO) cells, Baby Hamster Kidney (BHK) cells, CV monkey kidney Origin defective Simian virus 40 (COS) cells and hybridoma cells.

14. The process according to claim 1, wherein the cell culture medium is a serum-free medium.

15. The process according to claim 1, wherein the recombinant polypeptide is coagulation factor VIII.

16. The process according to claim 15, wherein the recombinant coagulation factor VIII is a deletion derivative of full-length factor VIII with retained coagulant activity.

17. The process according to claim 16, wherein the deletion derivative of factor VIII is deletion derivative recombinant factor VIII SQ (r-VIII SQ).

18. A method of cultivating cells expressing a recombinant human polypeptide in a cell culture medium, comprising cultivating the cells in a cell culture medium comprising an inhibitor of metal-dependent proteases containing a phosphoramidate, hydroxamate or carboxylate, or an inhibitor of chymotrypsins containing α-(2-iminohexahydro-4(S)-pyrimidyl)-S-glycine, or a combination thereof.

19. A method of producing a recombinant human polypeptide, comprising cultivating cells expressing the polypeptide by the method according to claim 18, and recovering the polypeptide.

* * * * *

UNITED STATES PATENT AND TRADEMARK OFFICE
CERTIFICATE OF CORRECTION

PATENT NO.   : 5,851,800
DATED        : December 22, 1998
INVENTORS    : Lars Adamson et al It is certified that error appears in the above-identified patent and that said Letters Patent is hereby corrected as shown below:

Claim 10, column 12, line 43, after "inhibitor", insert --of--.

Signed and Sealed this

Eighth Day of June, 1999

Attest:

Q. TODD DICKINSON

*Attesting Officer*   Acting Commissioner of Patents and Trademarks